(12) United States Patent
Edic et al.

(10) Patent No.: US 8,111,803 B2
(45) Date of Patent: Feb. 7, 2012

(54) METHOD FOR ENERGY SENSITIVE COMPUTED TOMOGRAPHY USING CHECKERBOARD FILTERING

(75) Inventors: Peter Michael Edic, Albany, NY (US); Colin Richard Wilson, Niskayuna, NY (US); Samit Kumar Basu, Newark, CA (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/432,225

(22) Filed: Apr. 29, 2009

(65) Prior Publication Data

US 2010/0278296 A1 Nov. 4, 2010

(51) Int. Cl.
*G01N 23/087* (2006.01)
*G21K 5/10* (2006.01)
*H05G 1/64* (2006.01)
(52) U.S. Cl. .............. 378/5; 378/53; 378/98.9; 378/146
(58) Field of Classification Search .............. 378/5, 53, 378/98.9, 146
See application file for complete search history.

(56) References Cited

U.S. PATENT DOCUMENTS

| | | | |
|---|---|---|---|
| 4,686,695 A | | 8/1987 | Macovski |
| 5,570,403 A | * | 10/1996 | Yamazaki et al. ............... 378/5 |
| 5,600,700 A | * | 2/1997 | Krug et al. ...................... 378/57 |
| 5,841,833 A | * | 11/1998 | Mazess et al. ................ 378/98.9 |
| 6,332,015 B1 | * | 12/2001 | Honda ........................ 378/98.11 |
| RE37,536 E | | 2/2002 | Barnes |
| 6,901,131 B2 | | 5/2005 | Edic et al. |
| 6,904,118 B2 | | 6/2005 | Wu et al. |
| 7,082,182 B2 | | 7/2006 | Zhou et al. |
| 7,372,934 B2 | | 5/2008 | De Man et al. |
| 7,412,026 B2 | | 8/2008 | Liu et al. |
| 7,426,260 B2 | * | 9/2008 | Cantu et al. .................. 378/98.8 |
| 7,593,762 B2 | * | 9/2009 | Yu ................................ 600/425 |
| 7,649,981 B2 | * | 1/2010 | Seppi et al. .................... 378/158 |

(Continued)

FOREIGN PATENT DOCUMENTS

DE 4209376 A1 9/1993

(Continued)

OTHER PUBLICATIONS

Alvarez et al., "Energy-Selective Reconstruction in X-Ray Computerized Tomography", Phys. Med. Biol., vol. 21, No. 5, pp. 733-744, 1976.

(Continued)

*Primary Examiner* — Edward Glick
*Assistant Examiner* — Thomas R Artman
(74) *Attorney, Agent, or Firm* — Fletcher Yoder

(57) ABSTRACT

Methods for energy-sensitive computed tomography systems that use checkerboard filtering. A method of enhancing image analysis of projection data acquired using a detector configured with a checkerboard filter includes disposing in a system a detector to receive a transmitted beam of X-rays traversing through an object, where the system is configured so the detector receives both high- and one of total- and low-energy projection data; receiving the high- and one of total- and low-energy projection data at the detector; and then estimating an effective atomic number of the object and/or processing the projection data so as to mitigate reconstruction artifacts. The present invention has been described in terms of specific embodiment(s), and it is recognized that equivalents, alternatives, and modifications, aside from those expressly stated, are possible and within the scope of the appended claims.

14 Claims, 6 Drawing Sheets

U.S. PATENT DOCUMENTS

| | | |
|---|---|---|
| 7,885,372 B2 * | 2/2011 | Edic et al. .................... 378/5 |
| 7,970,096 B2 * | 6/2011 | Pavlovich et al. ............ 378/5 |
| 2002/0191751 A1 | 12/2002 | Bogatu et al. |
| 2004/0102688 A1 | 5/2004 | Walker et al. |
| 2005/0228272 A1 | 10/2005 | Yu |
| 2007/0205367 A1 * | 9/2007 | Deman et al. ......... 250/363.02 |
| 2008/0247504 A1 | 10/2008 | Edic et al. |
| 2009/0147910 A1 * | 6/2009 | Edic et al. .................... 378/5 |

FOREIGN PATENT DOCUMENTS

| | | |
|---|---|---|
| EP | 1384440 A2 | 1/2004 |
| WO | WO96/35372 A2 | 11/1996 |

OTHER PUBLICATIONS

Novelty Search Report Dated Apr. 13, 2009.

\* cited by examiner

METHOD FOR ENERGY SENSITIVE COMPUTED TOMOGRAPHY USING CHECKERBOARD FILTERING

CROSS-REFERENCE TO CO-PENDING APPLICATIONS

This application is related in some aspects to commonly owned U.S. patent application Ser. No. 11/952,494, filed Dec. 7, 2007, entitled "System and Method For Energy Sensitive Computed Tomography," the entire contents of which are hereby incorporated by reference.

BACKGROUND

The invention relates generally to computed tomography, and more particularly to methods for energy sensitive computed tomography systems that use checkerboard filtering.

Typically, energy-sensitive computed tomography systems employ one of two techniques: acquiring projection data using dual-energy principles, which modulate the spectrum from the X-ray tube by selecting the operating voltage of the X-ray tube or by spectral filtering techniques, or utilizing detector technology to provide energy-sensitive measurements. In one example of the former technique, data is acquired from an object using two operating voltages of an X-ray source to obtain two sets of measured intensity data using different X-ray spectra, which are representative of the X-ray flux that impinges on a detector element during a given exposure time. In a latter technique, energy sensitive detectors such as, but not limited to, photon counting detectors and dual-layered detectors are used. In general, at least one data set is then processed to represent line integrals of the linear attenuation coefficients of the object along paths of X-ray radiation from the source to the individual detector elements. The measured data that are processed are typically called projections. By using reconstruction techniques, cross-sectional images of the scanned object are formulated from the projections. Utilizing both sets of projection data acquired using different X-ray spectra, line integrals of the density distribution within the field of view of the imaging system of two chosen basis materials can be generated. By using reconstruction techniques, cross-sectional images of the density distributions for both basis materials can be formulated or the effective atomic number distribution within the field of view of the imaging system computed.

X-ray beam attenuation caused by a given length of a material, such as, but not limited to, bone or soft tissue, may be represented by an attenuation coefficient for that material. The attenuation coefficient models separate physical events that occur when the X-ray beam passes through a given length of the material. A first event, known as Compton scatter, denotes the tendency of an X-ray photon, passing through the length of the material, to be scattered or diverted from an original beam path, with a resultant change in energy. A second event, know as photoelectric absorption, denotes the tendency of an X-ray photon, passing through the length of the material, to be absorbed by the material. There are other physical processes that may occur, but given the X-ray energies present in the spectra, their effect is insignificant relative to the two events listed above.

Different materials differ in the scatter and absorption properties, resulting in different attenuation coefficients. In particular, the probability of Compton scattering depends in part on the electron density of the imaged particle and probability of photoelectric absorption depends in part on atomic number of the imaged material, i.e., the greater the atomic number, the greater the likelihood of absorption. Furthermore, both Compton scattering and photoelectric absorption depend in part on the energy of the X-ray beam. As a result, materials can be distinguished from one another based upon relative importance of photoelectric absorption and Compton scattering effects in X-ray attenuation by the material. A density distribution and an effective atomic number distribution may be obtained using the two sets of projection data. However, the technique has limitations due to a slow acquisition mechanism since projection data sets corresponding to two separate energy spectra from the X-ray tube must be measured. This limitation can be overcome by rapidly alternating the operating voltage of the X-ray tube at alternating view angle positions of the rotating gantry; however, this technique requires special circuitry in the power supply to enable sufficient switching speeds.

Using dual-energy techniques, a density distribution and an effective atomic number distribution may be obtained using the two sets of projection data. However, the technique has limitations due to a slow acquisition mechanism since projection data sets corresponding to two separate energy spectra from the X-ray tube must be measured. This limitation can be overcome by rapidly alternating the operating voltage of the X-ray tube at alternating view angle positions of the rotating gantry; however, this technique requires special circuitry in the power supply to enable sufficient switching speeds.

Projection data acquisition for energy sensitive computed tomography (CT) may be implemented using various techniques that typically involve modification of X-ray generation or X-ray detection. For example, Rotate-Rotate dual-energy acquisitions (e.g., X-ray tube voltage modification on subsequent rotations of the CT gantry), fast-kVp switching of the X-ray tube voltage (i.e., X-ray tube voltage modulation at a periodicity driven by the particular imaging application), dual-layer detectors (i.e., variable X-ray detection) and energy sensitive X-ray detection (e.g., energy sensitive, photon-counting detectors) are such techniques.

Rotate-Rotate dual energy acquisitions require scanning of a volume using two operating voltages of the X-ray tube on subsequent gantry rotations. As a result, axial scanning protocols are required (obviating helical scanning techniques) to ensure comparable X-ray path integrations of the linear attenuations coefficients for both spectra. Since two sequential scans are required, overall scan times are increased with this technique.

"Fast-kVp switching" utilizes rapid switching between two operating voltages of the X-ray tube during scanning, which requires that special circuits be used to transfer stored charge in the high-voltage cable and transformer to enable rapid switching of the X-ray tube voltage.

Some dual-energy detectors use multiple detector layers; the top layer measuring a low-energy spectrum and the bottom layer measuring a high-energy spectrum. As a result, detector cost is effectively doubled. Dual-layered detectors are not cost effective since two separate detectors are needed to generate the requisite projection data.

Energy sensitive detectors detect individual X-ray photons and characterize their energy so that the spectral distribution of the measured spectrum is estimated. The detector cannot accurately measure the spectrum from regions of an object with minimal attenuation as signal pile-up occurs, due to limitations in counting rates provided with current technology.

While all these technologies have identifiable limitations, some provide better fidelity in spectral sensitivity than others. For example, dual-layer detectors provide moderate fidelity in spectral sensitivity; dual-energy acquisition and X-ray tube voltage switching provide good fidelity; while energy-sensitive detectors typically provide the best fidelity in spectral sensitivity. A good metric to evaluate energy sensitive techniques is the separation in mean energy of energy sensitive measurements. As the difference in mean energy increases, the fidelity in spectral sensitivity increases.

Some energy sensitive techniques reduce throughput (dual energy scanners, photon counting detectors) or require more costly hardware (fast kVp switching, dual-layer detectors). Therefore, it is desirable to employ techniques that maintain throughput, allow generation of high-resolution CT imagery that use all of the acquired projection data (i.e., both high and full-spectrum data), and provide the requisite fidelity in spectral sensitivity.

BRIEF DESCRIPTION

In accordance with an embodiment of the invention, a method of enhancing image analysis is provided. The method of enhancing image analysis of projection data acquired using a detector configured with a checkerboard filter includes disposing in a system a detector to receive a transmitted beam of X-rays traversing through an object, wherein said system is configured so said detector receives high- and one of total- and low-energy projection data; receiving high- and one of total- and low-energy projection data at the detector; and at least one of: estimating an effective atomic number of the object; and processing the projection data to mitigate reconstruction artifacts.

In accordance with another embodiment of the invention, a method of energy-sensitive computed tomography imaging is provided. The method of energy-sensitive computed tomography imaging includes disposing an X-ray source to emit an X-ray beam; disposing an object positioned within the X-ray beam; disposing a detector to receive a transmitted beam of the X-rays traversing through the object; disposing a filter comprising a pattern of attenuating material between the X-ray source and the detector, the filter configured to facilitate measurement of projection data that can be used to generate high-energy and one of low-energy and total-energy spectral information; and estimating an effective atomic number of the object.

In accordance with another embodiment of the invention, a method of energy-sensitive computed tomography imaging is provided. The method of energy-sensitive computed tomography imaging includes disposing an X-ray source to emit an X-ray beam; disposing an object positioned within the X-ray beam; disposing a detector to receive a transmitted beam of the X-rays traversing through the object; disposing a filter comprising a pattern of attenuating material between the X-ray source and the detector, the filter configured to facilitate measurement of projection data that can be used to generate high-energy and one of low-energy and total-energy spectral information; and processing the projection data to mitigate reconstruction artifacts.

These and other advantages and features will be more readily understood from the following detailed description of preferred embodiments of the invention that is provided in connection with the accompanying drawings.

DETAILED DESCRIPTION

As discussed in detail below, embodiments of the invention include a method for energy-sensitive computed tomography using checkerboard filtering. The computed tomography method disclosed herein may employ a computed tomography system that uses a checkerboard filter that can economically provide desired spectral information of an object. The methods allow for an alternative means to measure energy-sensitive projection data suitable for material decomposition and effective atomic number estimation. Additionally, since the spectral data is measured at each view angle position, only a single scan is required to measure the requisite spectral projection data information, as is needed for dual-energy acquisition. In this manner, this checkerboard filtering approach and method facilitates both helical and axial scanning protocols. However, since adjacent detector cells measure different spectral information, special processing steps are needed for both high-resolution CT number reconstruction and energy sensitive CT processing. High-resolution CT number reconstruction may be needed for inspection techniques, such as for parcel and luggage screening. Aspects of this invention can prove useful to provide energy-sensitive CT information for explosive detection system, as an example. The methods disclosed herein can be applicable, however, to any type of CT inspection system (e.g., parcels, luggage, etc.). Although not explicitly stated here, the techniques disclosed herein can be applied to any X-ray imaging technique: computed tomography, X-ray projection imaging, X-ray tomosynthesis/laminography imaging, and the like. Additional advantages with embodiments of the invention include a minimal impact to existing imaging mechanics (e.g., X-ray tube, detector, data acquisition system, etc.); facilitation of both helical and axial imaging scenarios; and, generation of high-resolution CT number image and high fidelity energy sensitive CT information.

Figure 1:
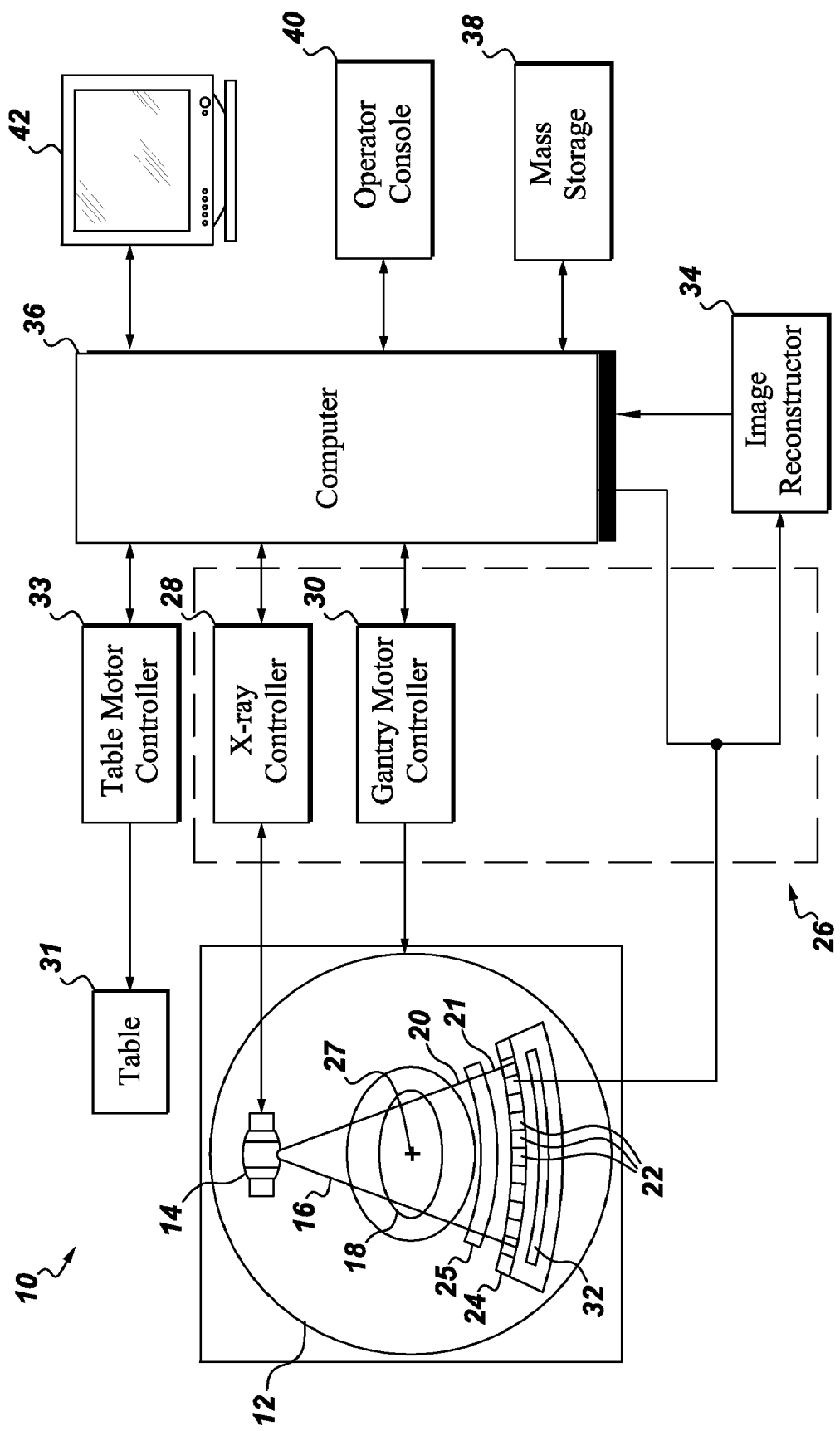
FIG. 1 is a block diagram representation of a computed tomography system using a checkerboard filter in accordance with an embodiment of the invention.

FIG. 1 is a block diagram representation of a computed tomography system 10. The system 10 includes a gantry 12 having an X-ray source 14 configured to emit an X-ray beam 16 responsive to electrons impinging upon a target material therein. In an example, the X-ray source 14 is an X-ray tube. In another embodiment, the X-ray source operates at a maximum operating voltage between about 60 to about 200 kV. In yet another embodiment, the maximum operating voltage can be as high as 450 kV. The X-ray beam is incident upon an object 18 resulting in a transmitted X-ray beam 20 through the object 18. Non-limiting examples of the object 18 include a human being, an animal, baggage, and industrial parts. The transmitted X-ray beam 20 through the object 18 is further incident upon filter 25 resulting in a filtered X-ray beam 21 which impinges upon a detector 24. The detector 24 includes one or more rows or columns of detector elements 22 that produce electrical signals that represent the intensity of the transmitted beam 21. The electrical signals are acquired and processed to reconstruct an image of the features within the object 18.

Figure 2:
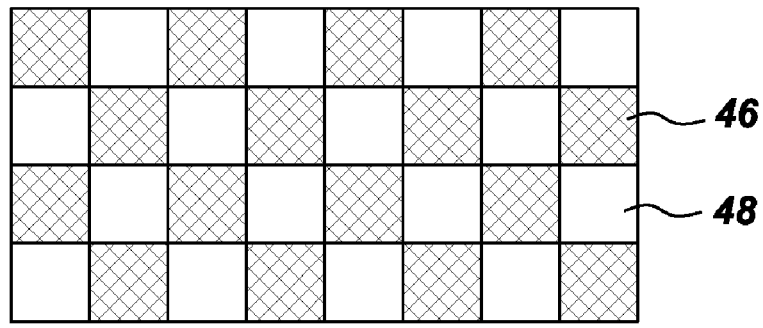
FIG. 2 is a schematic illustration of a checkerboard filter from the computed tomography system of FIG. 1 in accordance with an embodiment of the invention.

A filter 25 having a pattern of multiple attenuation materials such as high-attenuation materials and low-attenuation materials, is disposed between the X-ray source 14 and the detector 24 and outputs a high-energy spectrum in patterned sections containing attenuating material 46 and a total energy spectrum in the patterned regions of little or no attenuating material 48 as shown in FIG. 2. The term "high-energy spectrum" is used to denote an energy spectrum that has a relatively higher mean energy. The terms "total-energy spectrum" or "full-energy spectrum" are used to denote energy spectra that have a relatively lower mean energy in reference to the high-energy spectrum. In the description that follows, the filter 25 comprises alternating sections of attenuating material 46 placed between sections with no attenuating material 48; however, both sections may comprise attenuating material of differing attenuating properties depending on the desired shaping of the X-ray spectrum. In an example, the high-energy spectrum includes a maximum energy between about 80 to about 200 keV. In an alternative embodiment, the high-energy spectrum includes a maximum energy as high as 450 keV. The filter 25 includes filtering sections arranged alternately such that a high-energy spectrum is outputted when the transmitted radiation 20 passes through pixels with the filtering sections 46, while a total spectrum of the radiation 20 passes through pixels without filtering sections 48. The term checkerboard as used herein does not mean solely matching the pattern of a gameboard used in the popular game of checkers but also includes meaning any arrangement of differing filtering or attenuating material(s) on the filter 25. For example, the term also entails layouts and patterns including alternating by row, by column, a bull's-eye type configuration, random pattern, and the like. Additionally, the term low attenuation material herein includes the use of no attenuation material in certain embodiments. Thus, while embodiments of the non-filtering sections 48 are shown with no filtering or attenuating material(s), other embodiments of the non-filtering sections 48 may merely have lower attenuating properties than those in the filtering sections 46.

Rotation of the gantry 12 around a center of rotation 27 and the operation of X-ray source 14 are governed by a control system 26. The control system 26 includes an X-ray controller 28 that provides power and timing signals to the X-ray source 14, a gantry motor controller 30 that controls the rotational speed and position of the gantry 12, and a table motor controller 33 that controls motion of a table 31. An image reconstructor 34 receives sampled and digitized X-ray data from a data acquisition system 32 and performs high-speed reconstruction. The reconstructed image is applied as an input to a computer 36, which stores the image in a mass storage device 38. The image reconstructor 34 may be part of the computer 36, or may be a remote system.

The computer 36 also receives commands and scanning parameters from an operator via a console 40, which has some form of operator interface, such as a keyboard, mouse, voice activated controller, or any other suitable input apparatus. An associated display 42 allows the operator to observe the reconstructed image and other data from the computer 36. The operator supplied commands and parameters are used by the computer 36 to provide control signals and information to the data acquisition system 32, the X-ray controller 28, the gantry motor controller 30, and table motor controller 33. The table motor controller may comprise a table, or a conveyor belt with inline scanning devices.

Further, the computer 36 records a pair of intensity data measured by alternating detector elements 22 and processed by data acquisition system 32 corresponding to a total-energy spectrum and the high-energy spectrum respectively. The computer 36 also interpolates the intensity data of at least one of the high-energy spectrum and the total-energy spectrum to obtain interpolated intensity measurements used to generate projection data at a spatial sampling inherent with the original detector configuration. In one embodiment, the high-energy spectrum and the total-energy spectrum are used in subsequent processing steps. Further, in one embodiment, the computer 36 subtracts the interpolated intensity data of the high-energy spectrum from the total-energy spectrum to obtain intensity data corresponding to a low-energy spectrum. Further, in an alternate embodiment, the computer 36 subtracts the high-energy spectrum from the interpolated total-energy spectrum to obtain intensity data corresponding to a low-energy spectrum. In yet another alternate embodiment, the computer 36 subtracts the interpolated high-energy spectrum from the interpolated total-energy spectrum to obtain intensity data corresponding to a low-energy spectrum. Additionally, in an alternate embodiment, the computer 36 uses one of the total-energy spectrum and the interpolated total-energy spectrum as an estimate of the low-energy spectrum. Material decomposition and effective atomic number estimation of the object 18 are calculated based upon the projection data generated from measurements from the high-energy spectrum and one of the total-energy spectrum and the low-energy spectrum. In the text that follows, the total-energy spectrum and the low-energy spectrum, which can be computed from the high- and total-energy spectrum, are used interchangeably since both denote a spectrum with a lower mean energy. Further details of the calculations can be found in co-pending application Ser. No. 11/690245, entitled "System and Method of Density and Effective Atomic Number Imaging", filed on Mar. 23, 2007, and assigned to the same assignee as this application, the entirety of which is incorporated by reference herein. Although discussed with reference to computer 36, the measured projection data can be processed by other computing hardware that is either local to or remote to the imaging system 10.

It should be noted that embodiments of the invention are not limited to any particular computer for performing the processing tasks of the invention. The term "computer," as that term is used herein, is intended to denote any machine capable of performing the calculations, or computations, necessary to perform the tasks of the invention. The term "computer" is intended to denote any machine that is capable of accepting a structured input and of processing the input in accordance with prescribed rules to produce an output. It should also be noted that the phrase "configured to" as used herein means that the computer is equipped with a combination of hardware and software for performing the tasks of the invention, as will be understood by those skilled in the art.

Figure 3:
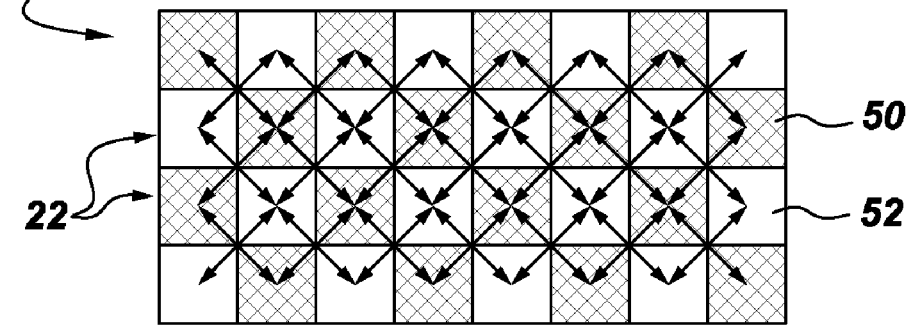
FIG. 3 is a schematic illustration of a detector array identifying data locations beneath the checkerboard filter in FIG. 2 that undergo a portion of a method in accordance with an embodiment of the invention.
Figure 5:
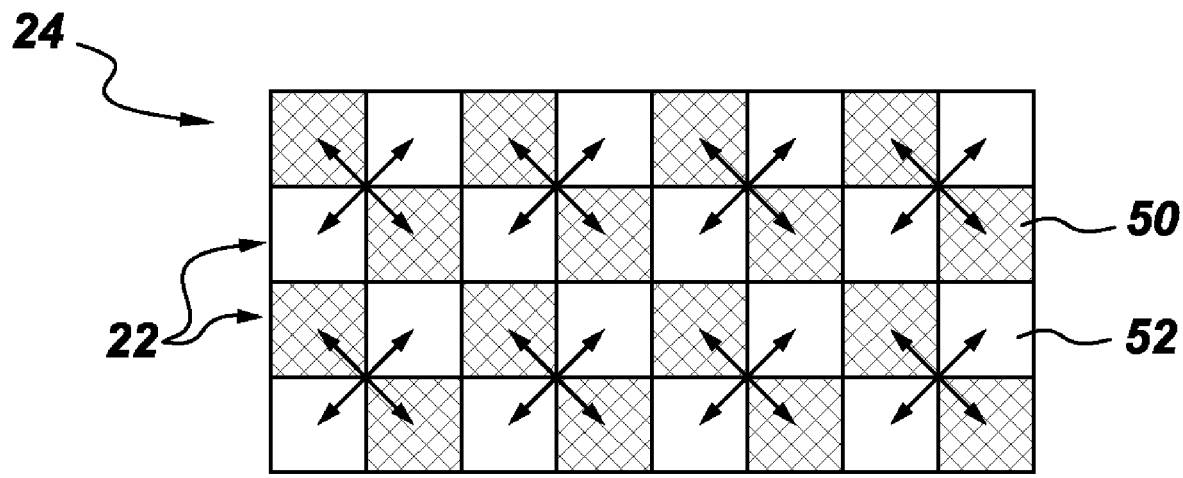
FIG. 5 is a schematic illustration of a detector array identifying data locations beneath the checkerboard filter in FIG. 2 that undergo a method in accordance with another embodiment of the invention.

FIG. 2 is a schematic illustration of the filter 25 used as the checkerboard filter according to an embodiment of the present invention. The filter 25 includes filtering sections 46 arranged alternately in a checkerboard pattern such that X-ray intensity data passing through these sections correspond to the high-energy spectrum that is distinct from intensity data corresponding from the total-energy spectrum that pass through the non-filtering sections 48. In an exemplary embodiment, the pattern is chosen to align with boundaries of individual detector elements 22 (FIGS. 1, 3, 5). The pattern is also referred to as a pixel-to-pixel checkerboard pattern. Filter materials may be high atomic number sections or layers deposited or applied to the top surface of the detector or to a plastic sheet that is positioned between the X-ray source 14 and the detector 24. The high atomic number layers can be a metal layer that has desired X-ray attenuation properties for the detector pixels used to measure the high-energy spectral information. In an alternative embodiment, the high atomic number layers may include a K-edge filter leveraging interaction of photons with the K-shell electrons of the material to appropriately shape the spectrum.

FIGS. 3-6 are schematic illustrations of a detector 24, or detector array, undergoing a method for energy-sensitive computed tomography using checkerboard filtering in accordance with various embodiments of the invention. The detector 24 is undergoing effective Z preprocessing steps in the figures. Since adjacent detector 22 cells "see" different X-ray spectra and have different path trajectories through the object being scanned and imaged, the trajectories cannot be used directly with material decomposition techniques. The material decomposition techniques require identical X-ray path trajectories for the high and low-energy spectral information. In order to address this issue, the method can average the projection or intensity data from nearby detector cells 50 measuring high-energy spectral information and will average the projection or intensity data from nearby detector cells 52 measuring lower or total-energy spectral information. This approach mitigates different X-ray path trajectories since the same process is applied for both the high- and low-energy projection data estimation.

Figure 4:
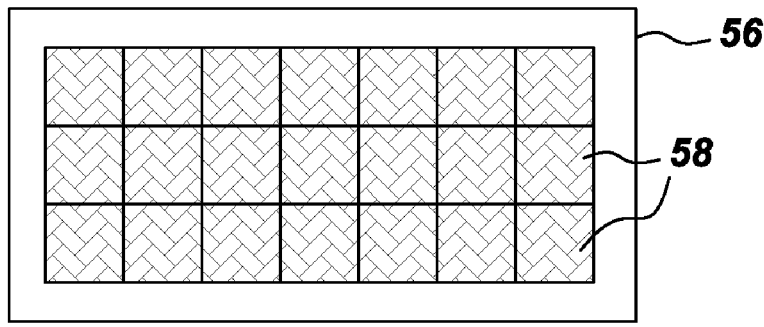
FIG. 4 is a schematic illustration of the resulting virtual detector array using data from the detector shown in FIG. 3 undergoing additional portions of the method in accordance with an embodiment of the invention.

There are several ways under the present invention for conducting the nearby detector cell averaging step. In an embodiment, the projection data in diagonal detector cells 50 for high-energy spectral information is averaged; and, similarly, the projection data in diagonal detector cells 52 for low-, or total-energy spectral information is also averaged. FIGS. 3 and 4 depict sequential illustrations of the detector cells 22 undergoing an embodiment of this averaging process. As shown, projection data is estimated at the original sampling interval, but at an intermediate spacing relative to the originally acquired projection data (i.e., ½ detector offset both laterally and vertically). The original detector footprint 56 is shown in relation to the offset detectors cells 58.

Figure 6:
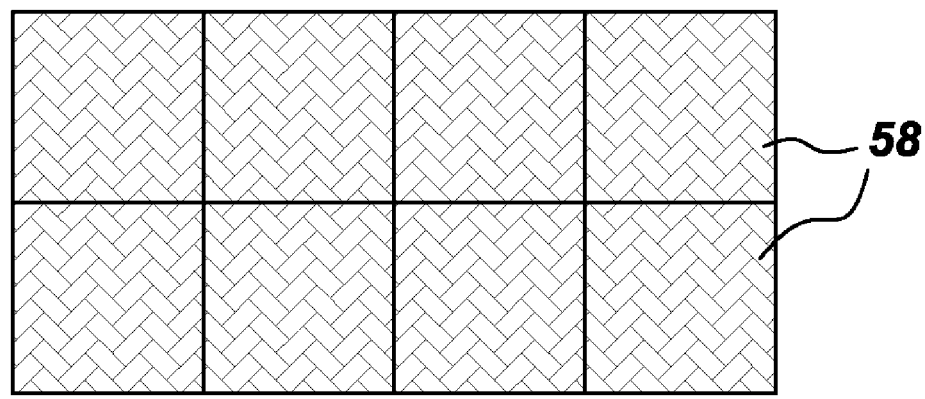
FIG. 6 is a schematic illustration of the resulting virtual detector array using data from the detector shown in FIG. 5 undergoing additional portions of a method in accordance with an embodiment of the invention.

FIGS. 5 and 6 depict sequential illustrations of the detector cells 22 of the detector 24 undergoing the averaging process in another embodiment. The sampling of the projection data is reduced by a factor of 2. The averaging of diagonal pixels 50, 52 results in spacing at 2× pitch of the resolution detector cells 58 of the original detector 24.

The processing steps described herein reduce the inherent resolution of the imaging systems since data interpolation steps are employed. In some instances, the reduced resolution is not a concern when estimating the effective atomic number for large objects. However, it would be beneficial to devise techniques that recover the original resolution of the imaging system. For resolution recovery processing, signal processing techniques can be employed to mitigate reconstruction artifacts. The measured projection data acquired using the checkerboard filter technique results in projection data that appears to be corrupted with a high-frequency spectrally-dependent signal. The corruption is actually the difference between the measured projection values for high- and one of total- or low-energy spectra. The corruption is at the Nyquist frequency of the sampled projection data (i.e., the highest frequency signal component that is allowed to exist or is discernable in the data). In an embodiment, this signal component is significantly reduced by using a high-order notch filter that is substantially at, or near, the Nyquist frequency. The resultant filtered projection data has projection values between high- and low-energy (total-energy) measurements, yet the undesirable high-frequency signal characteristics are drastically reduced. This allows for the reconstruction of high-fidelity, high-resolution CT number images.

Figure 7:
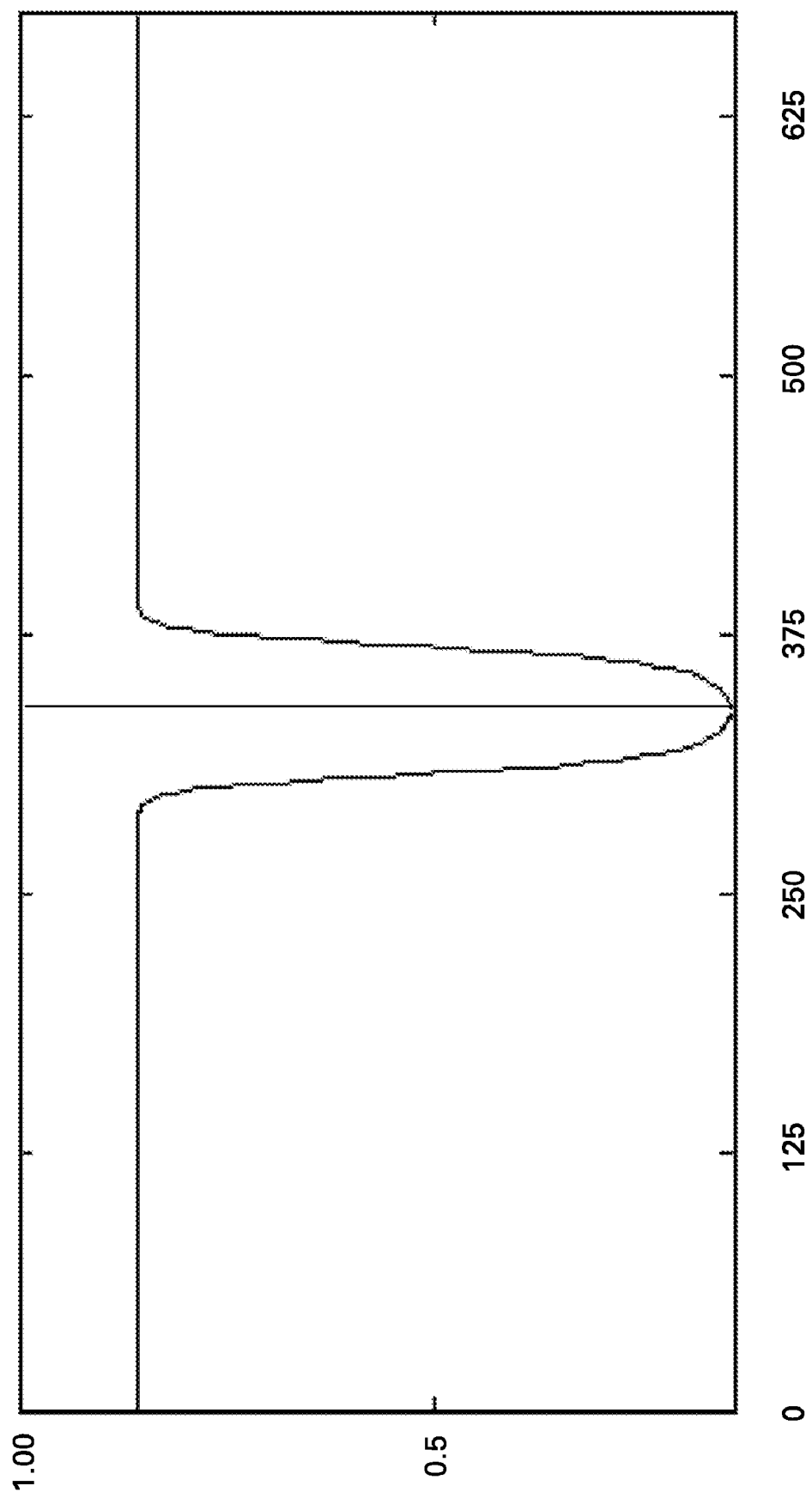
FIG. 7 is a Fourier Transform of the windowing function used with the reconstruction kernel in accordance with an embodiment of the invention.

FIG. 7 depicts a Fourier Transform of a windowing function used in conjunction with the reconstruction kernel that is known in the art, which is essentially a filter. In one embodiment, this function is multiplied by the Fourier Transform of the reconstruction kernel so as to modify the frequency characteristics of the reconstructed image. As shown, the x-axis is an index relating to the discrete spatial frequencies; and, the y-axis shows a scaling factor. Thus, when the windowing function=1, the reconstruction kernel frequency response is not modified. When the windowing function<1, the reconstruction kernel frequency response is reduced.

Figure 8:
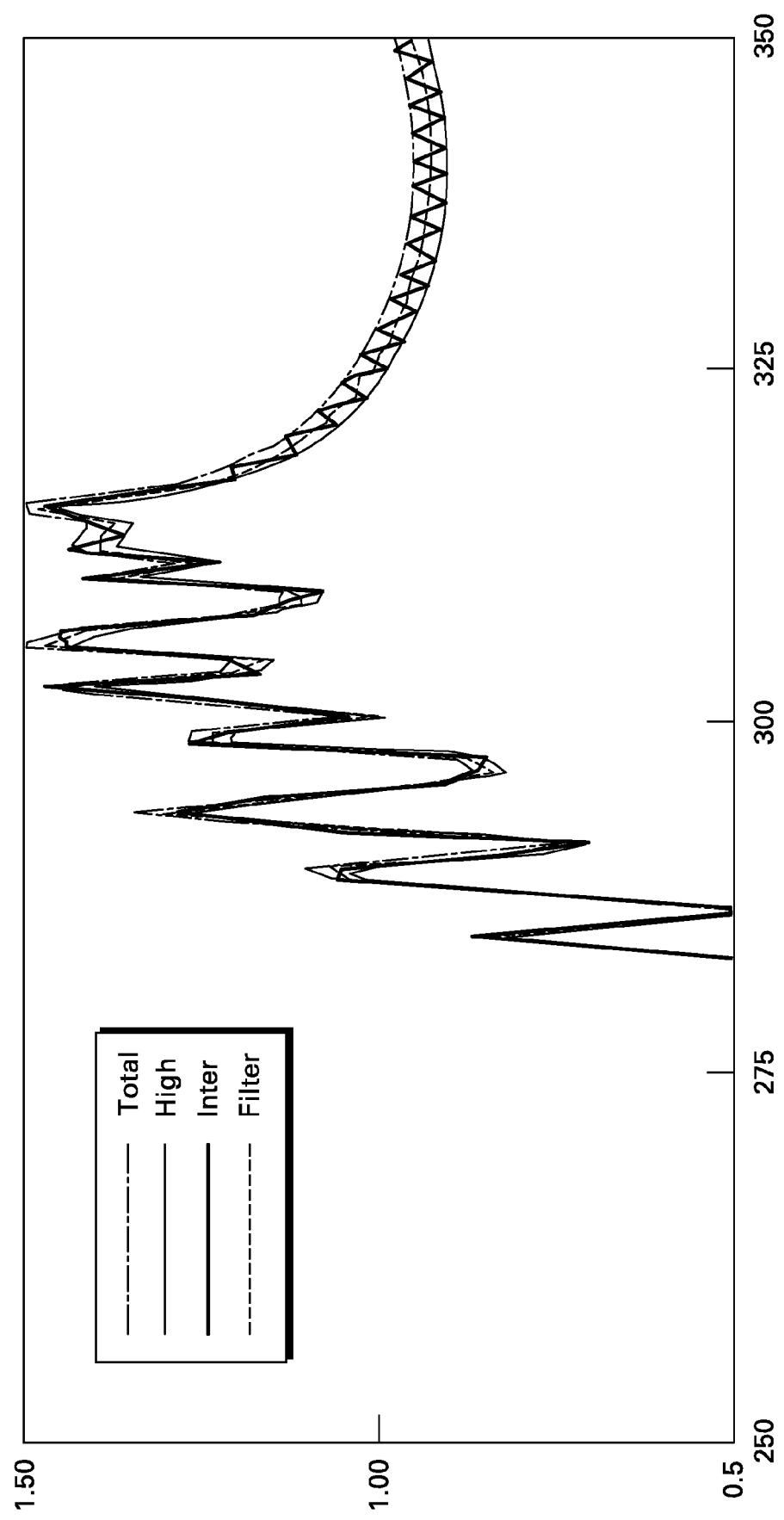
FIG. 8 is a collection of profiles of projection data in accordance with an embodiment of the invention.

FIG. 8 depicts exemplary profiles of simulated projection data. As shown, the x-axis is an index relating to the detector cell number; and, the y-axis is a line integral of linear attenuation coefficient (i.e., what the CT data acquisition process measures). As the legend in FIG. 8 indicates, the intermittent dotted line entitled "Total" is a plot of projection data acquired using the full (e.g., unfiltered) spectrum. The solid line entitled "High" is a plot of projection data acquired using the high-energy (e.g., filtered) spectrum. The darker solid line entitled "Inter" is a plot of projection data acquired using the detector 24 with the checkerboard filter 25 placed in front of the detector. The dashed line entitled "Filter" is a plot of the filtered projection data that results from the application of the window function, in the Fourier Domain to the projection data, prior to using the unmodified reconstruction kernel. In an alternative embodiment, the reconstruction kernel and windowing function may be combined into a single filter. In another alternative embodiment, the windowing function may be implemented by a data interpolation step in the frequency domain, as is the case when using Fourier-domain reconstruction techniques. As understood by those skilled in the art, the filtering techniques described herein can be implemented in the measurement space (spatial dimension) using convolution principles or in the frequency space (spatial frequency dimension) using processing techniques to achieve the same effect.

Advantageously, embodiments of the invention provide a simultaneous acquisition of high-spectrum data and total-spectrum data, thereby facilitating high-throughput system configurations. Moreover, the system is cost effective and does not require expensive electronics as compared to alternative techniques. Further, the detector does not require limiting the absolute flux intensity of incident radiation as is commonly needed in systems using photon-counting detectors since standard energy-integrating detector technology can be utilized to measure the high-energy and total-energy signals.

Figure 9:
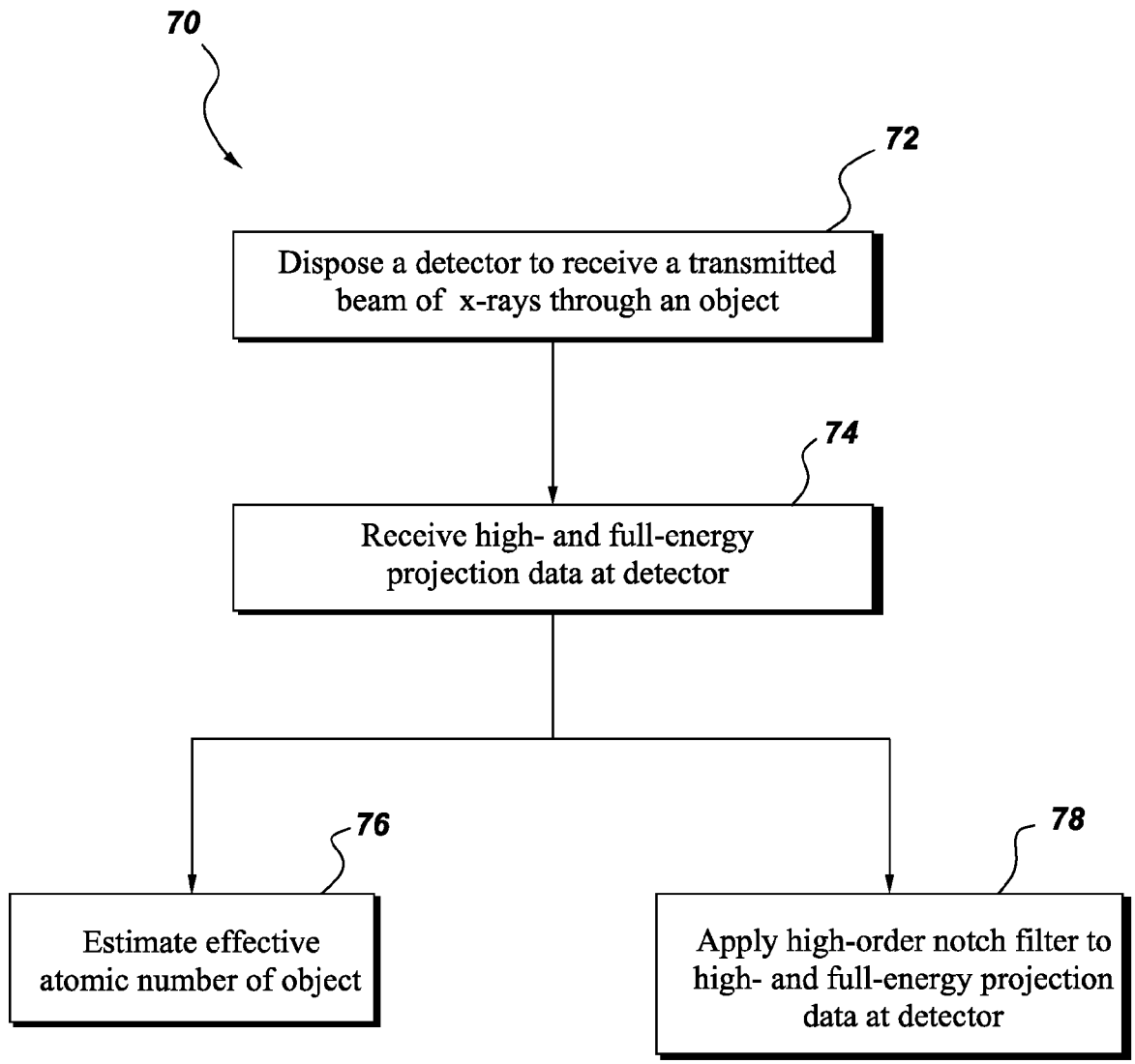
FIG. 9 is a flow chart representing a method for energy-sensitive computed tomography using checkerboard filtering in accordance with an embodiment of the invention.

FIG. 9 is a flow chart representing a method for energy-sensitive computed tomography using checkerboard filtering in accordance with an embodiment of the invention. The method 70 includes disposing in a system a detector to receive a transmitted beam of X-rays traversing through an object 72, wherein said system is configured so said detector receives high- and full-energy projection data at 74. The method then either estimates an effective atomic number of the object at 76 and/or applies processing on the projection data to mitigate reconstruction artifacts at 78. In an alternative embodiment the method 70 may both estimates an effective atomic number of the object at 76 and apply processing on the projection data to mitigate reconstruction artifacts at 78.

The various embodiments of a method for energy-sensitive computed tomography using checkerboard filtering described herein thus provide a way to generate a high-resolution CT number image using all of the acquired projection data and a way to estimate the effective atomic number with the scanned volume. Further, the system that employs this technique allows for a cost-effective means of imaging avoiding expensive electronics.

Therefore, according to one embodiment of the present invention, a method of enhancing image analysis of projection data acquired using a detector configured with a checkerboard filter includes disposing in a system a detector to receive a transmitted beam of X-rays traversing through an object, wherein said system is configured so said detector receives high- and one of total- and low-energy projection data; receiving high- and one of total- and low-energy projection data at the detector; and at least one of: estimating an effective atomic number of the object; and processing the projection data to mitigate reconstruction artifacts.

According to another embodiment of the present invention, a method of energy-sensitive computed tomography imaging, includes disposing an X-ray source to emit an X-ray beam; disposing an object positioned within the X-ray beam; disposing a detector to receive a transmitted beam of the X-rays traversing through the object; disposing a filter comprising a pattern of attenuating material between the X-ray source and the detector, the filter configured to facilitate measurement of projection data that can be used to generate high-energy and one of low-energy and total-energy spectral information; and estimating an effective atomic number of the object.

According to another embodiment of the present invention, a method of energy-sensitive computed tomography imaging, includes disposing an X-ray source to emit an X-ray beam; disposing an object positioned within the X-ray beam; disposing a detector to receive a transmitted beam of the X-rays traversing through the object; disposing a filter comprising a pattern of attenuating material between the X-ray source and the detector, the filter configured to facilitate measurement of projection data that can be used to generate high-energy and one of low-energy and total-energy spectral information; and processing the projection data to mitigate reconstruction artifacts.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments for measuring energy sensitive information. For example, the use of a photon-counting detector with respect to one embodiment can be adapted for use with a filter having an alternating row pattern described with respect to another. Similarly, the various X-ray source and detector features for energy sensitive projection data measurement described above, as well as other known equivalents for each feature, can be mixed and matched with the checkerboard filtering techniques by one of ordinary skill in this art to construct additional systems and techniques in accordance with principles of this disclosure. Furthermore, the checkerboard filter is described as being proximate to the detector; however, the checkerboard filter can be positioned anywhere between the X-ray source and the detector.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A method of enhancing image analysis of projection data comprising:
    transmitting a beam of X-rays through an object toward a detector such that the beam of X-rays passes through a filter comprising alternating regions of high attenuation material and low attenuation material prior to reaching the detector;
    simultaneously acquiring high-energy projection data at a first set of locations on the detector and lower-energy projection data at a second, different set of locations on the same detector, wherein the high-energy projection data corresponds to those X-rays passing through the high attenuation material of the filter, and the lower-energy projection data corresponds to those X-rays passing through the low attenuation material of the filter;
    computing a respective average of the high-energy projection data for each detector element where high energy projection data was not measured by averaging the high-energy projection data measured at adjacent diagonal detector elements to the respective detector element where high energy projection data was not measured;
    computing a respective average of the lower-energy projection data for each detector element where lower energy projection data was not measured by averaging the lower-energy projection data measured at adjacent diagonal detector elements to the respective detector element where lower energy projection data was not measured; and
    at least one of:
        estimating an effective atomic number of the object based on the high-energy and lower-energy projection data; or
        processing the projection data to mitigate reconstruction artifacts based on the high-energy and lower-energy projection data.

2. The method of claim 1, wherein the detector elements measuring high-energy projection data are disposed in a checkerboard pattern in relationship to detector cells receiving lower-energy projection data.

3. The method of claim 1 wherein the processing comprises employing one of projection-domain filtering, Fourier-domain filtering, and data interpolation.

4. The method of claim 1, wherein a pattern defined by the alternating regions of the filter aligns with the boundaries of individual elements of the detector.

5. The method of claim 1, wherein the lower energy projection data comprises total energy projection data or low energy projection data.

6. The method of claim 1, wherein the object comprises a human being, an animal, baggage, or industrial part.

7. A method of energy-sensitive computed tomography imaging, comprising:
   emitting an X-ray beam from an X-ray source through an object;
   receiving the X-ray beam on a detector after the X-ray beam has passed through a filter comprising alternating regions of high attenuation material and low attenuation material such that X-rays passing through the high attenuation material strike different portions of the same detector as X-rays passing through the low attenuation material, wherein the X-rays passing through the high attenuation material and the X-rays passing through the low attenuation material are simultaneously incident on the detector;
   computing a respective average of the high-energy projection data for each detector element where high energy projection data was not measured by averaging the high-energy projection data measured at adjacent diagonal detector elements to the respective detector element where high energy projection data was not measured; and
   computing a respective average of the lower-energy projection data for each detector element where lower energy projection data was not measured by averaging the lower-energy projection data measured at adjacent diagonal detector elements to the respective detector element where lower energy projection data was not measured; and
   estimating an effective atomic number of the object based on a set of high-energy projection data corresponding to the X-rays that pass through the high attenuation material and on a set of lower-energy projection data corresponding to the X-rays that pass through the low attenuation material.

8. The method of claim 7, wherein the array of detector cells receiving high-energy projection data are disposed in an alternating pattern in relationship to detector cells receiving lower-energy projection data.

9. The method of claim 7, wherein a pattern defined by the alternating regions of the filter aligns with the boundaries of individual elements of the detector.

10. The method of claim 7, wherein the object comprises a human being, an animal, baggage, or industrial part.

11. A method of energy-sensitive computed tomography imaging, comprising:
    emitting an X-ray beam from an X-ray source through an object;
    receiving the X-ray beam on a detector after the X-ray beam has passed through a filter comprising alternating regions of high attenuation material and low attenuation material such that X-rays passing through the high attenuation material strike different portions of the same detector as X-rays passing through the low attenuation material, wherein the X-rays passing through the high attenuation material and the X-rays passing through the low attenuation material are simultaneously incident on the detector;
    computing a respective average of high-energy projection data for each detector element of the detector where high energy projection data was not measured by averaging the high-energy projection data measured at adjacent diagonal detector elements to the respective detector element where high energy projection data was not measured;
    computing a respective average of lower-energy projection data for each detector element of the detector where lower energy projection data was not measured by averaging the lower-energy projection data measured at adjacent diagonal detector elements to the respective detector element where lower energy projection data was not measured; and
    processing the projection data to mitigate reconstruction artifacts based on a set of high-energy projection data corresponding to the X-rays that pass through the high attenuation material and on a set of lower-energy projection data corresponding to the X-rays that pass through the low attenuation material.

12. The method of claim 11 wherein processing the projection data comprises employing one of projection-domain filtering, Fourier-domain filtering, and data interpolation.

13. The method of claim 11, wherein a pattern defined by the alternating regions of the filter aligns with the boundaries of individual elements of the detector.

14. The method of claim 11, wherein the object comprises a human being, an animal, baggage, or industrial part.

* * * * *